(12) United States Patent
Saeed (10) Patent No.: US 9,569,723 B2
(45) Date of Patent: Feb. 14, 2017

(54) METHOD OF CONTINUOUS PREDICTION OF PATIENT SEVERITY OF ILLNESS, MORTALITY, AND LENGTH OF STAY

(75) Inventor: Mohammed Saeed, Ann Arbor, MI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 581 days.

(21) Appl. No.: 13/883,766

(22) PCT Filed: Nov. 3, 2011

(86) PCT No.: PCT/IB2011/054884
§ 371 (c)(1),
(2), (4) Date: May 7, 2013

(87) PCT Pub. No.: WO2012/063166
PCT Pub. Date: May 18, 2012

(65) Prior Publication Data
US 2013/0232103 A1 Sep. 5, 2013

Related U.S. Application Data

(60) Provisional application No. 61/410,984, filed on Nov. 8, 2010.

(51) Int. Cl.
| G06Q 50/22 | (2012.01) |
| G06Q 50/24 | (2012.01) |
| G06K 9/62 | (2006.01) |
| G06N 5/00 | (2006.01) |
| G06F 19/00 | (2011.01) |

(52) U.S. Cl.
CPC .............. *G06N 5/003* (2013.01); *G06F 19/345* (2013.01); *G06F 19/3437* (2013.01); *G06K 9/62* (2013.01);
(Continued)

(58) Field of Classification Search
None
See application file for complete search history.

(56) References Cited

U.S. PATENT DOCUMENTS 5,724,983 A 3/1998 Selker et al.
6,317,731 B1 * 11/2001 Luciano .......................... 706/21
(Continued)

FOREIGN PATENT DOCUMENTS

| JP | 2008176473 A | 7/2008 |
| WO | 2007/054841 | 5/2007 |

OTHER PUBLICATIONS

Tu et al., Multicenter Validation of a Risk Index for Mortality, Intensive Care Unit Stay, and Overall Hospital Length of Stay After Cardiac Surgery. American Heart Association [online], 1995 [retrieved on Jan. 18, 2016] Retrieved from the Internet:<URL:http://www.google.com/url?sa=t&rct=j&q=&esrc=s&source=web&cd=4>.*
(Continued)

*Primary Examiner* — Ben Rifkin
*Assistant Examiner* — Nathan Brown, Jr.

(57) ABSTRACT

A method for predicting a patient's outcome variable, such as a probability of mortality/recovery, includes accessing at least one of a plurality past patients' data fields including physiological and/or laboratory data, and a time of stay indicating how long each patient had been under care at the time. An outcome variable estimation algorithm is generated by data mining from a plurality of past patients' physiological and/or laboratory data, corresponding time of stay, and associated outcome variables. A current patient's outcome variable is determined from the current patient's physiological and/or laboratory data, the current time of stay, and the outcome variable estimation algorithm.

18 Claims, 4 Drawing Sheets

(52) U.S. Cl.
CPC ............. *G06Q 50/22* (2013.01); *G06Q 50/24* (2013.01); *G01N 2800/52* (2013.01); *G06F 19/3431* (2013.01); *G06F 19/3443* (2013.01)

(56) References Cited

U.S. PATENT DOCUMENTS

| | | | |
|---|---|---|---|
| 2004/0010481 A1 | 1/2004 | Mani et al. | |
| 2004/0225201 A1 | 11/2004 | McNair | |
| 2007/0150307 A1 | 6/2007 | Lancaster et al. | |
| 2008/0009684 A1 | 1/2008 | Corsetti et al. | |
| 2008/0214904 A1 | 9/2008 | Saeed et al. | |
| 2009/0089092 A1 | 4/2009 | Johnson et al. | |
| 2009/0105550 A1 | 4/2009 | Rothman et al. | |

OTHER PUBLICATIONS

Woods et al., Evaluation of predicted and actual length of stay in 22 Scottish intensive care units using the Apache III system, Anaesthesia pp. 1058-1065 [online], 2000 [retrieved on Jan. 18, 2016]. Retrieved from the Internet:<URL:http://www.google.com/url?sa=t&rct=j&q=&esrc=s&source=web&cd=3&ved=0ahUKEwjdv_WBuLTKAhVW42MKHUrpBD0QFggrMAI>.*

Ramoni, et al. "Robust Outcome Prediction for Intensive-Care Patients", Methods of Information in Medicine, 2001; 40:39-45 © Schattauer GmbH (2001).

Gunderson, et al., "Using Within-Patient Correlation to Impove the Accuracy of Shock Outcome Prediction for Cardiac Arrest"; Resuscitation (2008) 78, 46-51.

Nimgaonkar, et al., "Prediction of Mortality in an Indian Intensive Care Unit: Comparison Between Apache II and Artificial Neural Networks", 2000 www.cse.iitb.ac.in/~sundarsha/Pubs-dir/mortality-prediction.ps.gz.

Cook, et al., "The Attributable Mortality and Length of Intensive Care Unit Stay of Clinically Important Gastrointestinal Bleeding in Critically Ill Pateients", Critical Care, Dec. 2001 V. 5, No. 6 pp. 368-375.

Pusajó, et al., "Postoperative Intra-abdominal Sepsis Requiring Reoperation", Arch Surg—vol. 128, Feb. 1993.

* cited by examiner

METHOD OF CONTINUOUS PREDICTION OF PATIENT SEVERITY OF ILLNESS, MORTALITY, AND LENGTH OF STAY

CROSS REFERENCE TO RELATED APPLICATIONS

This application is a national filing of PCT application Serial No. PCT/IB2011/054884, filed Nov. 3, 2011, published as WO 2012/063166 A1 on May 18, 2012, which claims the benefit of U.S. provisional application Ser. No. 61/410,984 filed Nov. 8, 2010, which is incorporated herein by reference.

The present application relates to a system or method for predicting outcome variables such as length of stay, mortality, need for specific therapy, and severity of illness of a patient in a health care environment. It finds particular application in improving and optimizing the prediction a patient's length of stay or probability of morality within a health care environment and will described with particular reference thereto. However, it will be appreciated that it is also applicable to intensive care units, post-anesthesia care unit, general care ward, rehabilitation unit, operating room, and the like.

Presently, patient recovery/mortality prediction systems, such as the SAPS (Simplified Acute Physiology) system, are typically run at a patient's time of admission. The patient's length of stay or probability of mortality is estimated by weighting a combination of several admission criteria including, admitting vital signals, prior chronic disease, therapeutic and diagnostic investigations, procedures (planned or unplanned surgeries), demographics (age and gender), and the like. A problem exists if the prediction routine is run after the first day of admission, the same routine and relative weighting of the various criteria are used as would have been used as if the patient had just been admitting on the later date.

The present inventor has observed that when predicting a patient's length of stay or probability of mortality after the patient has been under intensive care for several days, the prediction is less accurate. In clinical practice, the clinical ramifications of a failure to improve after receiving treatment(s) or a particular criteria, such as an abnormal value occurring several days into a hospital admission can have different significance relative to the condition on the first day of admission. For example, an abnormal serum bicarbonate level at the first day of admission may be due to a physiologic insult the patient suffered prior to coming to the hospital. However, if a patient were to develop severe abnormalities to a serum bicarbonate level several days into admission after intensive therapeutic and monitoring care, it may be surmised that the patient is in a critical state that could not be alleviated after several days of intensive care.

The present application provides a new and improved method and system for predicting outcome variables of a patient which overcomes the above-referenced problems and others, In accordance with one aspect, a method for predicting a patient's outcome variable is provided. At least one of a plurality past patients' data fields is accessed including physiological and/or laboratory data, and a time of stay indicating how long each patient had been under care at the time the physiological and/or laboratory data were generated and associated outcome variables from a clinical database. An outcome variable estimation algorithm is generated from the plurality past patients physiological and/or laboratory data, corresponding time of stay, and associated outcome variables.

In accordance with another aspect, a patient information device is provided. A controller receives physiological and/or laboratory data about a current patient from a patient monitoring device. A unit determines a time of stay indicative of a time that the current patient has been under care. A prediction unit predicts an outcome variable by applying an outcome variable estimation algorithm to the current patient's physiological and/or laboratory data using the determined time of stay.

In accordance with another with another aspect, a method of predicting a probability of outcome is provided. Physiological and/or laboratory data is measured for a current patient who is staying under care in a medical facility. A time of stay which the current patient has been staying under care in the medical facility is determined. The time of stay dependent outcome prediction algorithm is applied using the measured physiological and/or laboratory data and the determined time of stay to predict a probability of outcome.

One advantage resides in improved accuracy and quality of predicting a patient's length of stay or probability of morality.

Another advantage resides in the real-time update of the prediction of a patient's length of stay or probability of morality as new or revised input data becomes available throughout the stay of patient.

Another advantage resides in improved patient throughput.

Still further advantages of the present invention will be apparent to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
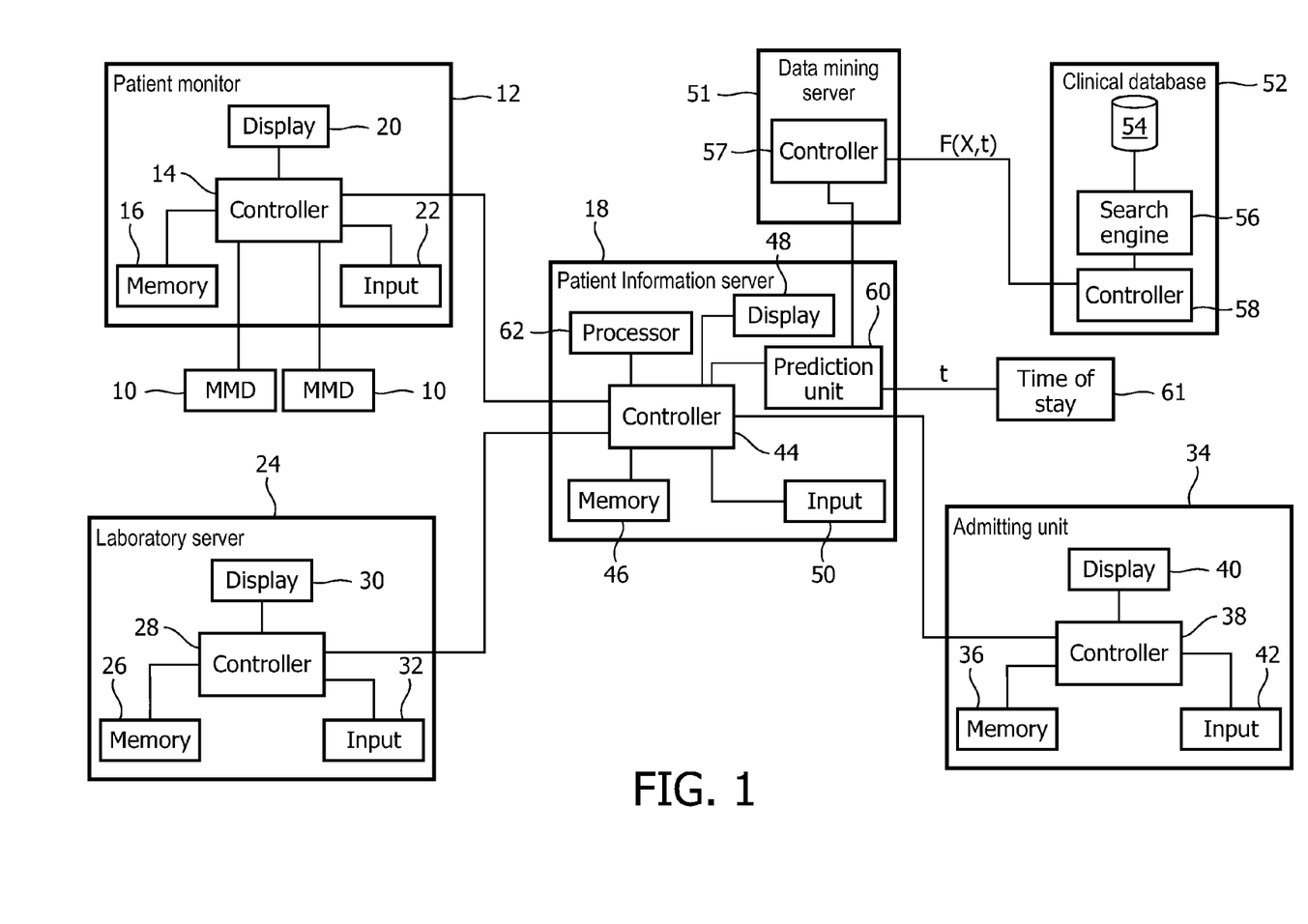
FIG. 1 is a diagrammatic illustration of a patient recovery/mortality prediction system in accordance with the present application.

With reference to FIG. 1, a patient (not shown) is monitored by various medical monitoring devices or sensors 10 that measure physiological parameters of the patient directly or in a lab and generate physiological data indicative thereof. These medical monitoring devices 10 may include an electrocardiographic (ECG) instrument with ECG electrodes, IV fluid pumps, blood pressure sensors, SpO2 sensors, pulse sensors, thermometers, respiratory sensors, exhaled gas sensors, and the like. Other medical monitoring devices 10 can be associated with a patient, and not all of the above-mentioned medical monitoring devices 10 have to be associated with a patient at any given time. It should be appreciated that while only two medical monitoring devices 10 are illustrated, more medical monitoring devices are contemplated. As used herein, medical monitoring devices signifies data sources indicating patient health, or the like. Electronics for receiving signals from the medical monitoring device 10 and for optionally performing signal processing on such signals are embodied in the illustrated embodiment as a multi-functional patient monitor device (PMD) 12, or may be embodied partly or wholly as on-board electronics disposed with one or more of the medical monitoring devices 10 or so forth. It should also be appreciated that the medical monitoring devices 10 and the PMD 12 could also be embodied into a single device. The PMD 12, for example, may be a monitor or monitoring system that travels with the patient, such as the transmitter of an ambulatory patient worn monitoring system, or the like.

In one embodiment, the medical monitoring devices 10 transmit the generated physiological data via a body coupled network, Bluetooth, wired or wireless network, or the like to a controller 14 of the PMD 12. The PMD 12 serves as a gathering point for the physiological data measured by the medical monitoring devices 10, and provides temporary storage for the data in a memory 16. The collected physiological data is concurrently transmitted to a controller 14 in the PMD 12 which then transmits the physiological data through a hospital network (not shown) to a patient information server 18 where the physiological data is displayed and stored. The controller 14 of the PMD 12 also controls a display 20 to display the measured physiological data received from each of the medical monitoring devices 10 in the corresponding PMD display 20. The PMD 12 also includes an input device 22 that allows the user, such as a system administrator, to view, manipulate, and/or interact with the data displayed on the display 18. The input device 20 can be a separate component or integrated into the display 18 such as with a touch screen monitor. The controller 14 may include a processor or computer, software, or the like.

A laboratory server 24 transmits laboratory data through the hospital network to the patient information server 18. The laboratory data may include white blood cell count data, serum potassium data, serum sodium data, serum bicarbonate data, bilirubin level data, and the like. Other laboratory data can be associated with a patient, and not all of the above-mentioned laboratory data have to be associated with a patient at any given time. As used herein, laboratory data signifies data sources indicating patient health, or the like.

The laboratory server 24 serves as a gathering point for the laboratory data measured by clinicians in the lab or through clinical analysis, and provides temporary storage for the data in a memory 26. The collected laboratory data is concurrently transmitted to a controller 28 in the laboratory server 24 which then transmits the laboratory data through a hospital network to a patient information server 18 where the laboratory data is displayed and stored. The controller 28 of the laboratory server 24 also controls a display 30 to display the collected laboratory data received from the clinicians in the lab or through clinical analysis in the display 30. The laboratory server 24 also includes an input device 32 that allows the user, such as a clinician, to input laboratory data, view, manipulate, and/or interface with the data displayed on the display 30. The input device 32 can be a separate component or integrated into the display 30 such as with a touch screen monitor. The controller 28 may include a processor or computer, software, or the like.

In one embodiment, an admitting unit 34 transmits patient data through the hospital network to the patient information server 18. The patient data includes the age of the patient, gender of the patient, chronic diseases of the patient, patient history, the type of admission, and the like. Other patient data can be associated with a patient, and not all of the above-mentioned patient data have to be associated with a patient at any given time. As used herein, patient data signifies data sources indicating general patient information, patient history, or the like.

The admitting unit 34 serves as a gathering point for the patient data collected by admitting personal, and provides temporary storage for the data in a memory 36. The patient data is concurrently transmitted to a controller 38 in the admitting unit 34 which then transmits the patient data through a hospital network to a patient server 18 where the patient data is displayed and stored. The controller 38 of the admitting unit 34 also controls a display 40 to display the collected patient data received from the admitting personal in the display 40. The admitting unit 34 also includes an input device 42 that allows the user, such as admitting personal, to input patient data, view, manipulate, and/or interface with the data displayed on the display 40. The input device 42 can be a separate component or integrated into the display 40 such as with a touch screen monitor. The controller 38 may include a processor or computer, software, or the like.

A controller 44 of the patient information server 18 receives the physiological data from the patient monitor 12, the laboratory data from the laboratory server 24, and the patient data from the admitting unit 34 and stores the physiological data, laboratory data, and the patient data in a memory 46. The controller then controls a display 48 of the patient information server 18 to display the physiological data, laboratory data, and the patient data received from the patient in the display 48. The patient information server also includes an input device 50 that allows the user, such as administrative personal, to view, manipulate, and/or interface with the data displayed on the display 48. The input device 50 can be a separate component or integrated into the display 48 such as with a touch screen monitor.

In one embodiment, a data mining server 51 is connected to a clinical database 52 such as a world server, a plurality of national servers, a plurality of regional servers, and a plurality of hospital servers, a local hospital servers or the like. The clinical database 52 includes a patient database 54 that stores past patient cases and studies including input data fields and associated outcome variables. The patient input data fields include one or more vital signs (including heart rate, blood pressure, respiration rate, oxygen saturation, body weight, other blood pressures, and the like), automated or user-input problem lists including chronic problems, acute admitting problems (chest pain, shortness of breath, altered mental status/confusion, abdominal pain, and the like), ICD-9 codes (or equivalent coded medical problems), clinical laboratory data, fluid-balance, medications, ventilator settings, subjective nursing assessment, results of imaging studies, patient demographics (age, gender, race/ethnic background), current time of stay in the hospital or ICU, and the like relating to patient cases and studies. The patient outcome variables include length of stay, mortality, or need for an intervention (medication, ventilation, hemodialysis or the like), and the like relating to the outcomes of the associated patient cases and studies. A search engine 56 searches the patient database 54 including a time of stay at which each vital sign or another time of stay dependant data field features of patient cases and studies to find correlations to requested input data fields and associated variable outcomes. The correlating patient cases and studies are then transmitted by the controller 58 to a controller 57 of the data mining server 51. The controllers 57, 58 may include a processor or computer, software, or the like.

The controller 57 of the data mining server 51 accesses and searches the clinical database 52 for a plurality of input data fields and associated outcome variables from past patient cases and studies. In one embodiment, the outcome variable estimation algorithm includes time of stay dependant scores or weighting factors for a patient recovery/mortality scoring system to properly weight the different criteria based on the time the patient been under care for a current medical event, has stayed in the hospital, been in intensive care, or the like.

In another embodiment, the controller, utilizes the input data fields, time of stay, and associated outcome variables from past patient cases and studies to develop an outcome variable estimation algorithm for predicting a current patient's outcome variables in real time from the patient's physiological data, laboratory data, and the patient data as it is made available throughout the patient's hospital stay.

Typically, the outcome variable prediction software, algorithm, or routine is stored in is carried on other tangible memory or a computer readable medium 46 for execution by the processor. Types of computer readable medium 46 include memory such as a hard disk drive, CD-ROM, DVD-ROM and the like. Other implementations of the processor are also contemplated. Display controllers, Application Specific Integrated Circuits (ASICs), and microcontrollers are illustrative examples of other types of component which may be implemented to provide functions of the processor. Embodiments may be implemented using software for execution by a processor, hardware, or some combination thereof.

A prediction unit or processor 60 of the patient information server 18 receives the outcome variable estimation or prediction program, software, algorithm, routine, or the like from the data mining server 51 directly or via a computer readable medium. The prediction processor is connected with a time of stay determining unit 61, processor, routine or means, which determines the time of stay of the current patient, i.e. the time since the current care started, admission to the hospital, or intensive care unit, or the like. The prediction processor 60 applies the outcomes variable estimation program, software, routine, or algorithm to the current patient physiological and/or laboratory data using the current time of stay to estimate or predict the outcome variable(s). When the outcome variables estimation program includes the generation of time of stay dependent weighting values or scores, the time of stay dependency is calculated based on the time the underlying input data field was last updated. The most recent or current outcome variable(s) is displayed on the display 48.

Figure 2:
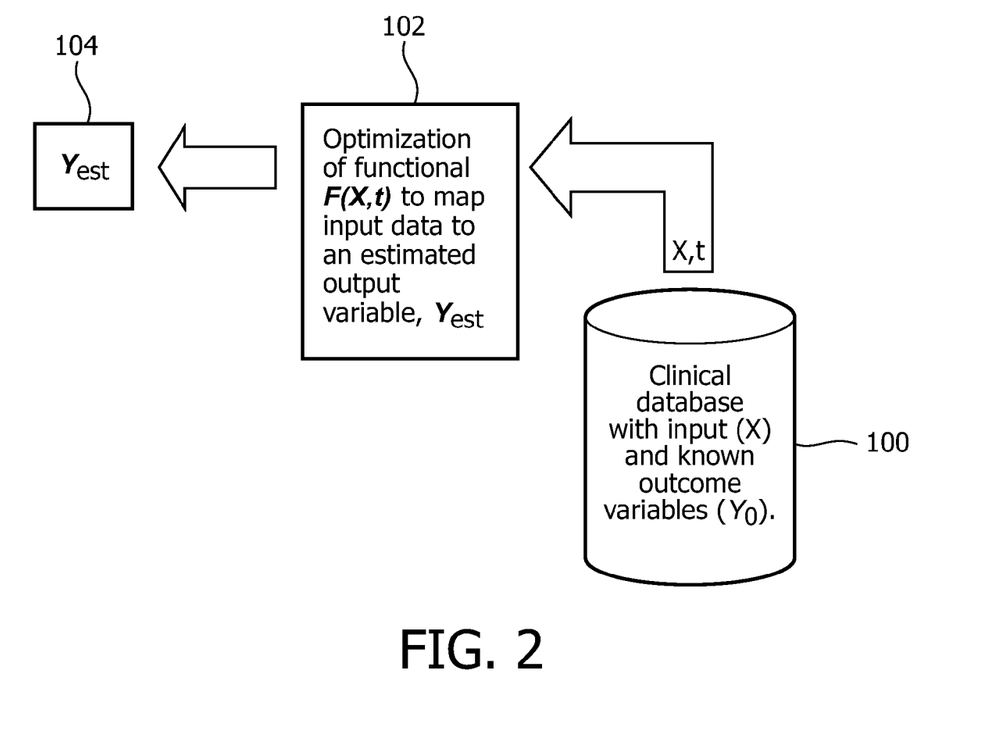
FIGS. 2-4 are diagrammatic illustrations of the operation of the patient information server in accordance with the present application.

With reference to FIG. 2, illustrated is a flowchart diagram for generating the outcome variable estimation algorithm. In a step 100, a clinical database is accessed and searched for a plurality of past input data fields X and associated past outcome variables $Y_0$. The past input data fields X and associated pasted outcome variables $Y_0$ from the past patient cases and studies are sourced in a plurality clinical databases including the contents of a world server, a plurality of national servers, a plurality of regional servers, and a plurality of hospital or local hospital servers.

In a step 102, the past input data fields X and past outcome variables $Y_0$ are used to develop the optimal function F(X,t) for predicting a current patient's outcome variables $Y_{est}$ from the patient's physiological data, laboratory data, and the patient data. The function F(X,t) can estimate an outcome variable $Y_o$ using the input data fields, X at any time, t, during a patient's hospital stay. The function can be identified by using several different methods including linear regression analysis, nonlinear regression analysis, neural networks, support vector machines, radial basis functions, expert rule-based, or classifier decision trees and the like.

In one embodiment, the determination of F(X,t), can utilize the input data fields, X, of a plurality of databases storing a collection of patients cases and studies, and the associated output variables, Yo, using multiple linear regression analysis such that the estimated outcome variables, $Y_{est}$. The estimated outcome variable, $Y_{est}$, is defined by:

$$Y_{est}=F(X,t)$$

where $$\min|Y_{est}-Y_o|$$

To find the function, F(X,t) that minimizes the differences between the estimated and observed outcomes in the training process, one can use one of several forms optimization techniques including least-squares estimation and gradient-searches. In the following example, K clinical data items are chosen from N different patients to create the input data vector, X. The associated observed (known) outcomes, Yo, from these N patients is noted by the vector, $[y_{o1} \ldots y_{oN}]^T$. For example, the outcome variable vector could equal a vector of the number of days each of the respective N patients stayed in the hospital or ICU. The predicted outcomes using the optimal function (defined by the vector $[b_{1,t} \ldots b_{K,t}]^T$) is noted by $Y_{est}$ (where $Y_{est}=[Y_{est1} \ldots Y_{estN}]$).

$$\begin{bmatrix} y_{est1} \\ y_{est2} \\ y_{est3} \\ y_{estN} \end{bmatrix} = \begin{bmatrix} x_{11} & x_{12} & x_{13} & x_{1K} \\ x_{21} & \ldots & \ldots & \ldots \\ x_{31} & \ldots & \ldots & \ldots \\ x_{N1} & X_{N2} & X_{N3} & X_{NK} \end{bmatrix} * \begin{bmatrix} b_{1,t} \\ b_{2,t} \\ b_{3,t} \\ b_{K,t} \end{bmatrix}$$

The least squares method is equivalent to finding the optimal vector for a point in time in the patient's stay, t, $[b_{1,t} \ldots b_{K,t}]^T$ such that the difference between the estimated outcomes, $Y_{est}$, $([y_{est1} \ldots y_{estN}]^T)$ and known outcomes, Yo $[Y_{o1} \ldots Y_{oN}]^T$ is minimal in a least squares sense for the N different patient records. Once the function, F(X,t), is determined for a specific outcome variable of interest, then it can be utilized to predict the desired outcome variable for a given current patient with known input data. A unique feature of this formula is the incorporation of the current hospital day, t, to find optimal formula for data provided from a given hospital day, t.

In a step 104, the function F(X,t) is identified for a various outcome variable and utilized to a predict, on a real time basis, the various outcome variables $Y_{est}$ including length of stay, mortality, or need for an intervention from the current patient's physiological data, laboratory data, and the patient data as it is made available throughout the hospital stay of the patient. In one embodiment, the outcome variable estimation algorithm is applied to a patient recovery/mortality scoring system to properly weight the different criteria based on the time the patient has stayed in the hospital and been under intensive care. In one embodiment, a function F(X,t) is developed for each day after admission (where t=0, 1, 2, 3 rounded to the ICU day).

As shown in the table below, a traditional patient health score is give for each specific finding of different variables relating to a patient's health. The patient health scores are related to a patient's health at the time of admission and do not take in account the time the patient spend in the hospital or the ICU. To account for the time the patient has been in the hospital or the ICU receiving intensive care, the outcome variable estimation algorithm is applied. The application of the outcome variable estimation algorithm properly weighs the patient health score with the amount of the time the patient has stayed in the hospital. The summation of the time of stay dependent scores provides an prediction of the outcome variable of the patient.

| Variable | Finding | Traditional Score (at adm.) | Score (time of stay) |
|---|---|---|---|
| Age in Years | <40 | 0 | F(t) |
|  | 40-59 | 7 | F(t) |
|  | 60-69 | 12 | F(t) |
|  | 70-74 | 15 | F(t) |
|  | 75-79 | 16 | F(t) |
|  | >=80 | 18 | F(t) |
| Heart Rate in BPM | <40 | 11 | F(t) |
|  | 40-69 | 2 | F(t) |
|  | 70-119 | 0 | F(t) |
|  | 120-159 | 4 | F(t) |
|  | >=160 | 7 | F(t) |
| Systolic Blood Pressure in mm HG | <70 | 13 | F(t) |
|  | 70-99 | 5 | F(t) |
|  | 100-199 | 0 | F(t) |
|  | >=200 | 2 | F(t) |
| Body Temperature in C. | <39 | 0 | F(t) |
|  | >=39 | 3 | F(t) |
| PaO2/FIO2 | <100 | 11 | F(t) |
|  | 100-199 | 9 | F(t) |
|  | >=200 | 6 | F(t) |
| Urinary output in L per 24 hours | <0.500 | 11 | F(t) |
|  | 0.500-0.999 | 4 | F(t) |
|  | >=1.000 | 0 | F(t) |
| Serum urea nitrogen in mg/dl | <28 | 0 | F(t) |
|  | 28-83 | 6 | F(t) |
|  | >=84 | 10 | F(t) |
| WBC count in 1000 per uL | <1.0 | 12 | F(t) |
|  | 1.0-19.9 | 0 | F(t) |
|  | >=20 | 3 | F(t) |
| Serum potassium in mEq/L | <3.0 | 3 | F(t) |
|  | 3.0-4.9 | 0 | F(t) |
|  | >=5.0 | 3 | F(t) |
| Serum sodium in mEq/L | <125 | 5 | F(t) |
|  | 125-144 | 0 | F(t) |
|  | >=145 | 1 | F(t) |
| Serum bicarbonate in mEq/L | <15 | 6 | F(t) |
|  | 15-19 | 3 | F(t) |
|  | >=20 | 0 | F(t) |
| Bilirubin level in mg/dl | <4.0 | 0 | F(t) |
|  | 4.0-5.9 | 4 | F(t) |
|  | >=6.0 | 9 | F(t) |
| Glasgow Coma Score | <6 | 26 | F(t) |
|  | 6-8 | 13 | F(t) |
|  | 9-10 | 7 | F(t) |
|  | 11-13 | 5 | F(t) |
|  | 14-15 | 0 | F(t) |
| Chronic diseases | Metasatic carcinoma | 9 | F(t) |
|  | Hematologic malignancy | 10 | F(t) |
|  | AIDS | 17 | F(t) |
| Type of Admission | Scheduled surgery | 0 | F(t) |
|  | Medical | 6 | F(t) |
|  | Unscheduled surgery | 8 | F(t) |

Figure 3:
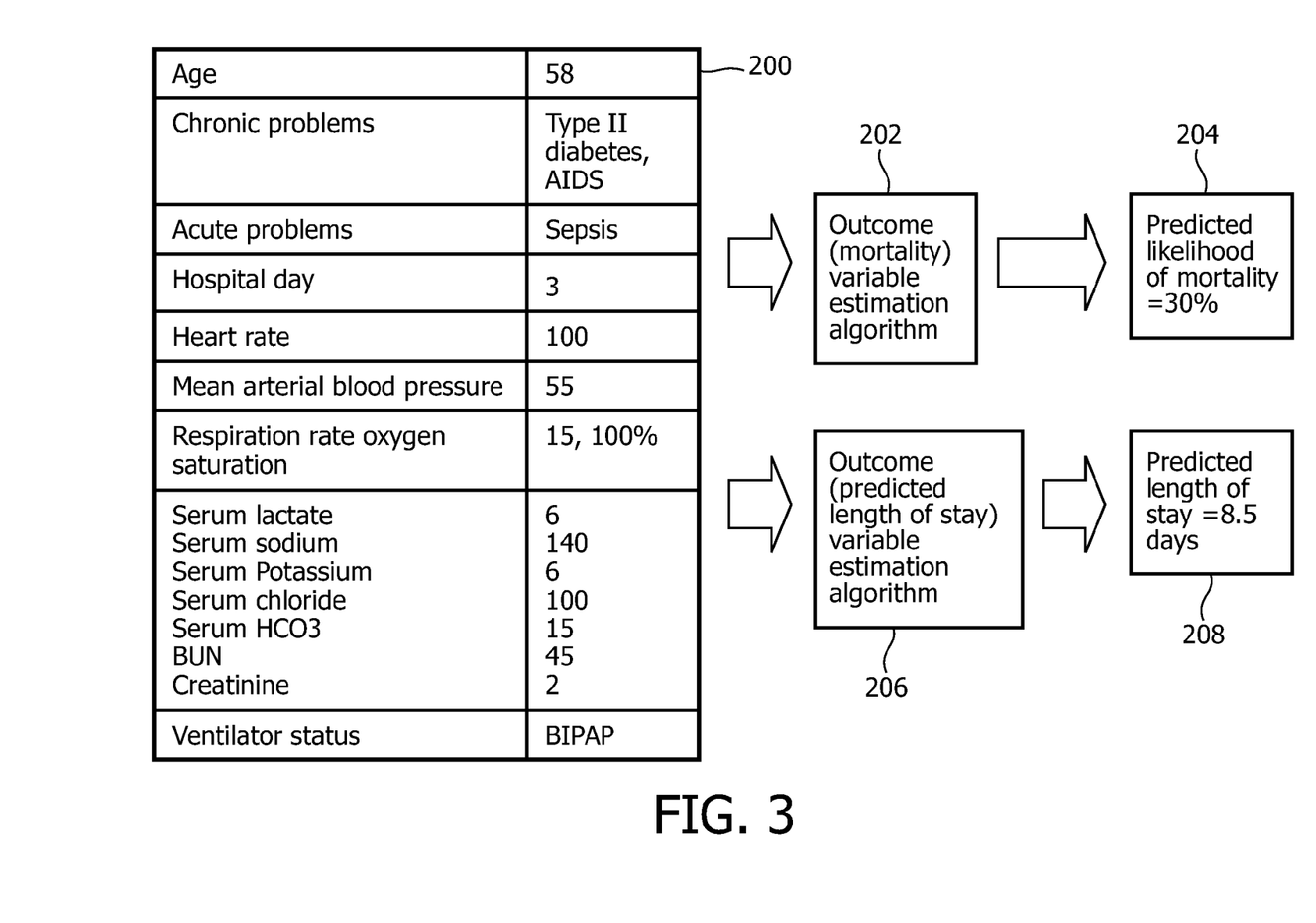

With reference to FIG. 3, illustrated is a flowchart diagram of the operation of the prediction unit. In a step 200, a current patient's physiological data, laboratory data, and the patient data are entered in a step 200. In a step 202, an outcome variable estimation algorithm, e.g. with time of stay dependant weighting values or scores, is used to determine the mortality of the patient. In a step 204, the patient's mortality is estimated to be 30% from the patient's physiological data, laboratory data, and the patient data. In a step 206, an outcome variable estimation algorithm is used to determine the length of stay of the patient. In a step 208, the patient's length of stay is estimated to be 8.5 days from the patient's physiological data, laboratory data, and the patient data.

Figure 4:
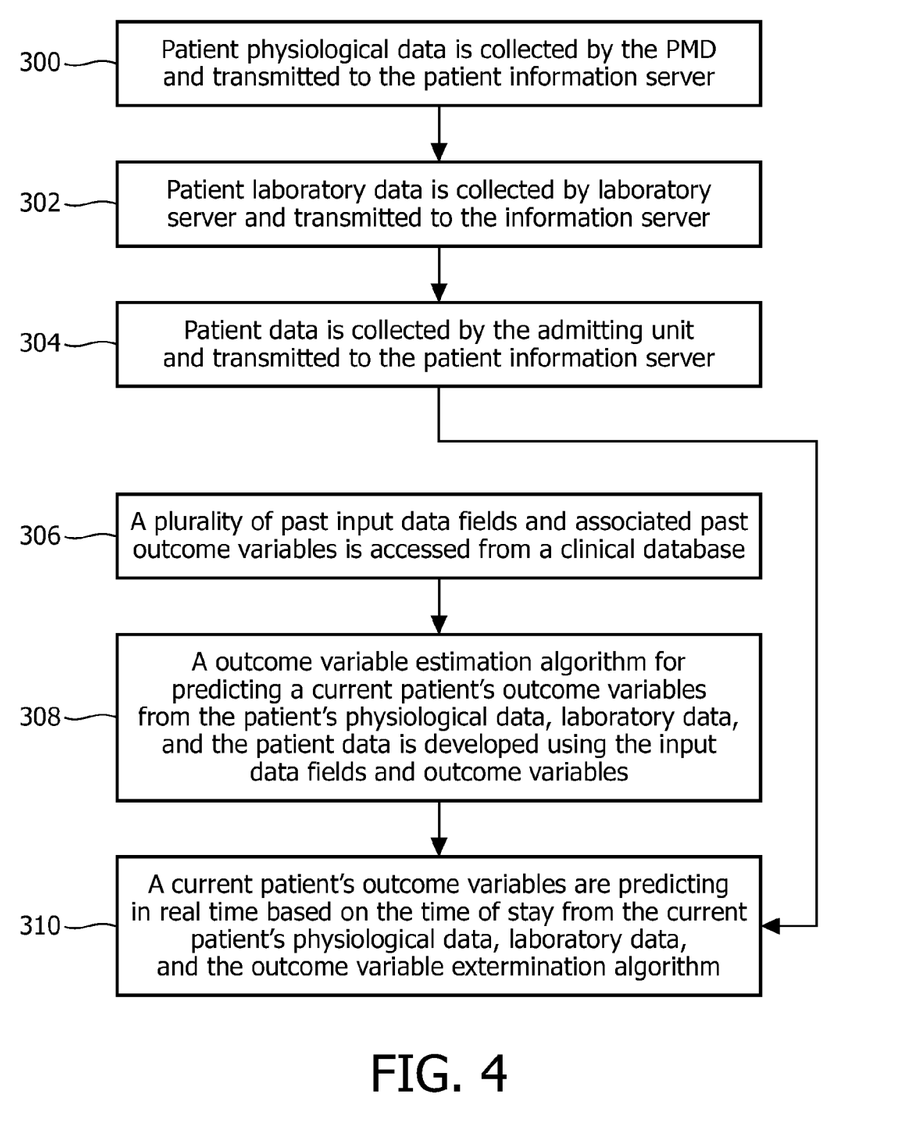

With reference to FIG. 4, illustrated is a flowchart diagram. In a step 300, patient physiological data is collected by the PMD and transmitted to the patient information server. In a step 302, patient laboratory data is collected by laboratory server and transmitted to the information server. In a step 304, patient data is collected by the admitting unit and transmitted to the patient information server. In a step 306, a plurality of past input data fields and associated past outcome variables is accessed from a clinical database. In a step 308, a variable outcome or prediction estimation algorithm for predicting a patient's outcome variables from the patient's physiological data, laboratory data, and the patient data is developed using the input data fields and outcome variables. In a step 310, a current patient's outcome variables are predicting in real time from the current patient's physiological data, laboratory data, time of stay, other patient input data fields and the outcome variable estimation algorithm.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A patient monitoring system comprising:
   a patient monitor device which collects physiological data from a patient;
   a control processor configured to:
      receive the collected physiological data from the patient monitor device,
      receive laboratory data about the patient from a laboratory,
      determine a time of stay indicative of a time the patient has been in a healthcare facility,
      predict an outcome variable continuously in real time by applying an outcome variable estimation algorithm to the patient's physiological and laboratory data using the determined time of stay.

2. The system according to claim 1, wherein the patient is in an intensive care unit (ICU) of the healthcare facility and the time of stay is indicative of a time the patient has been in the ICU and wherein the outcome variables include a predicted length of stay in the ICU and a probability of mortality.

3. The system according to claim 1, wherein the outcome variable estimation algorithm is generated by:
   accessing at least one of a plurality past patients' data fields including physiological and laboratory data, and a time of stay indicating how long each patient had been in the healthcare facility at the time the physiological and laboratory data were generated and associated outcome variables from a clinical database;
   generating the outcome variable estimation algorithm from the plurality past patients physiological and laboratory data, corresponding time of stay, and associated outcome variables.

4. The system according to claim 1, wherein the outcome variable estimation algorithm is generated using at least one of: linear regression analysis, nonlinear regression analysis, neural networks, support vector machines, radial basis functions, expert rule-based, and classifier decision trees.

5. The system according to claim 1, wherein the physiological data and the laboratory data include values indicative of the patient's health, wherein predicting the outcome variable by applying the outcome variable algorithm includes:

generating patient health scores for the values;

weighting each patient health score based on the determined time of stay; and combining the weighted scores, the combined weighted scores being indicative of the outcome variable.

6. The system according to claim 1, wherein the outcome variable algorithm is configured to calculate a Simplified Acute Physiology (SAP) score weighted based on the time of stay.

7. A patient monitoring system comprising:

a patient monitor device which collects physiological data from a patient;

a laboratory server configured to transmit laboratory data of the patient;

a control processor configured to:
  receive the collected physiological data from the patient monitor device,
  receive the laboratory data of the patient from the laboratory,
  determine a time of stay indicative of a time the patient has been in a healthcare facility,
  predict an outcome variable by applying an outcome variable estimation algorithm to the patient's physiological and laboratory data using the determined time of stay.

8. A patient monitoring system comprising:

a patient monitor device configured to collect physiological data from a patient;

a control processor configured to:
  receive the collected physiological data from the patient monitor device,
  receive the laboratory data of the patient from the laboratory,
  determine a time of stay indicative of a time the patient has been in a healthcare facility, predict an outcome variable by applying an outcome variable estimation algorithm to the patient's physiological and laboratory data using the determined time of stay; and a display configured to display the predicted outcome variable.

9. A method for predicting a patient's outcome variable, the method comprising, with one or more processors:

accessing at least one of a plurality past patients' data fields including physiological and laboratory data, and a time of stay indicating how long each patient had been in a healthcare facility at the time the physiological and laboratory data were generated and associated outcome variables from a clinical database;

generating a outcome variable estimation algorithm from the plurality past patients physiological and laboratory data, corresponding time of stay, and their associated outcome variables;

receiving a current patient's physiological and laboratory data;

determining the current patient's current time of stay in a healthcare facility; and applying the outcome variable estimation algorithm to the current patient's physiological and laboratory data and the current time of stay to estimate the current patient's probability of outcome continuously in real time; and controlling a display monitor to display a current probability of outcome.

10. The method according to claim 9, wherein the outcome variables include at least a probability of mortality.

11. The method according to claim 9, wherein in the past patient data fields include one or more vital signs, automated or user-input problem lists including chronic problems, acute admitting problems, clinical laboratory data, medications, subjective nursing assessment, patient demographics, and current length of stay in a hospital under intensive care.

12. The method according to claim 9, wherein the past patient associated outcome variables include time of stay, recovery/mortality, and intervention.

13. The method according to claim 9, wherein the outcome variable estimation algorithm is identified using at least one of: linear regression analysis, nonlinear regression analysis, neural networks, support vector machines, radial basis functions, expert rule-based, and classifier decision trees.

14. A non-transitory computer readable medium containing software which when loaded into one or more processors programs the one or more processors to perform the method according to claim 9.

15. A method of predicting a probability of outcome, comprising:

measuring physiological and laboratory data for a current patient who is staying under intensive care in a medical facility;

determining a time of stay which the current patient has been staying under intensive care in the medical facility;

applying a time of stay dependent outcome prediction algorithm using the measured physiological and laboratory data and the determined time of stay to predict a probability of recovery/mortality; and controlling a display device to display the probability of recovery/mortality.

16. A non-transitory computer readable medium containing software which when loaded into a processor programs the processor to perform the method according to claim 15.

17. A processor programmed to perform the method according to claim 15.

18. The method according to claim 15, wherein predicting the probability of recovery/mortality includes:

assigning scores to the measured physiological and laboratory data;

weighting the scores based on a current time of stay under intensive care; and combining the weighted scores to generate an acuity score indicative of the probability of recovery/mortality.

* * * * *